US012599557B2

(12) United States Patent
Tseng et al.

(10) Patent No.: US 12,599,557 B2
(45) Date of Patent: Apr. 14, 2026

(54) LIPOSOMAL SUSTAINED-RELEASE COMPOSITIONS CONTAINING A THERAPEUTIC DRUG AND USE THEREOF

(71) Applicants: TLC BIOPHARMACEUTICALS, INC., South San Francisco, CA (US); TAIWAN LIPOSOME CO., LTD., Taipei (TW)

(72) Inventors: Yun-Long Tseng, Taipei (TW); Hsin-Yi Chiu, Taipei (TW)

(73) Assignees: TLC BIOPHARMACEUTICALS, INC., South San Francisco, CA (US); TAIWAN LIPOSOME CO., LTD., Taipei City (TW)

( * ) Notice: Subject to any disclaimer, the term of this patent is extended or adjusted under 35 U.S.C. 154(b) by 825 days.

(21) Appl. No.: 17/605,367

(22) PCT Filed: Apr. 25, 2020

(86) PCT No.: PCT/US2020/029980
§ 371 (c)(1),
(2) Date: Oct. 21, 2021

(87) PCT Pub. No.: WO2020/220000
PCT Pub. Date: Oct. 29, 2020

(65) Prior Publication Data
US 2022/0211621 A1 Jul. 7, 2022

Related U.S. Application Data

(60) Provisional application No. 62/838,571, filed on Apr. 25, 2019.

(51) Int. Cl.

| | |
|---|---|
| *A61K 9/127* | (2025.01) |
| *A61K 31/045* | (2006.01) |
| *A61K 31/085* | (2006.01) |
| *A61K 31/135* | (2006.01) |
| *A61K 31/137* | (2006.01) |
| *A61K 31/167* | (2006.01) |
| *A61K 31/192* | (2006.01) |
| *A61K 31/196* | (2006.01) |
| *A61K 31/245* | (2006.01) |
| *A61K 31/397* | (2006.01) |
| *A61K 31/40* | (2006.01) |
| *A61K 31/405* | (2006.01) |
| *A61K 31/4168* | (2006.01) |
| *A61K 31/439* | (2006.01) |
| *A61K 31/445* | (2006.01) |
| *A61K 31/46* | (2006.01) |

(Continued)

(52) U.S. Cl.
CPC ............ *A61K 9/127* (2013.01); *A61K 31/045* (2013.01); *A61K 31/085* (2013.01); *A61K 31/135* (2013.01); *A61K 31/137* (2013.01); *A61K 31/167* (2013.01); *A61K 31/192* (2013.01); *A61K 31/196* (2013.01); *A61K 31/245* (2013.01); *A61K 31/397* (2013.01); *A61K 31/40* (2013.01); *A61K 31/405* (2013.01); *A61K 31/4168* (2013.01); *A61K 31/439* (2013.01); *A61K 31/445* (2013.01); *A61K 31/46* (2013.01); *A61K 31/4745* (2013.01); *A61K 31/485* (2013.01); *A61K 31/5415* (2013.01); *A61K 31/5513* (2013.01); *A61K 31/5517* (2013.01); *A61K 31/573* (2013.01); *A61K 31/616* (2013.01); *A61K 47/24* (2013.01); *A61K 47/28* (2013.01)

(58) Field of Classification Search
CPC .... A61K 9/127; A61K 31/045; A61K 31/085; A61K 31/135; A61K 31/137; A61K 31/167; A61K 31/192; A61K 31/196; A61K 31/245; A61K 31/397; A61K 31/40; A61K 31/405; A61K 31/4168; A61K 31/439; A61K 31/445; A61K 31/46; A61K 31/4745; A61K 31/485; A61K 31/5415; A61K 31/5513; A61K 31/5517; A61K 31/573; A61K 31/616; A61K 47/24; A61K 47/28
See application file for complete search history.

(56) References Cited

U.S. PATENT DOCUMENTS

2015/0064114 A1* 3/2015 Park ...................... A61K 31/44 600/431
2021/0100791 A1 4/2021 Shimoyama et al.

FOREIGN PATENT DOCUMENTS

CN 101199505 A * 6/2008
CN 105163720 A 12/2015

(Continued)

OTHER PUBLICATIONS

Patent machine translation for CN-101199505-A (Year: 2008).*
Karumanchi et al.; Rational design of liposomes for sustained release drug delivery of bevacizumab to treat ocular angiogenesis; Elsevier; Journal of Drug Delivery Science and Technology 47 (2018) 275-282 (Year: 2018).*

(Continued)

*Primary Examiner* — Robert A Wax
*Assistant Examiner* — John W Lippert, III
(74) *Attorney, Agent, or Firm* — Finnegan, Henderson, Farabow, Garrett & Dunner LLP

(57) ABSTRACT

Provided is a liposomal sustained-release composition comprising a therapeutic agent and one or more lipids. The therapeutic agent and total lipids are present in the liposomal sustained-released composition at a predetermined ratio. The liposomal sustained-release composition achieves a desired therapeutic effect while avoiding undesired side effects. The therapeutic agent is stably entrapped in the liposomes of the composition and sustainably released therefrom. This liposomal formulation for the therapeutic agent demonstrates an improved release profile.

17 Claims, 3 Drawing Sheets

(51) Int. Cl.

| | |
|---|---|
| ***A61K 31/4745*** | (2006.01) |
| ***A61K 31/485*** | (2006.01) |
| ***A61K 31/5415*** | (2006.01) |
| ***A61K 31/5513*** | (2006.01) |
| ***A61K 31/5517*** | (2006.01) |
| ***A61K 31/573*** | (2006.01) |
| ***A61K 31/616*** | (2006.01) |
| ***A61K 47/24*** | (2006.01) |
| ***A61K 47/28*** | (2006.01) |

(56) References Cited

FOREIGN PATENT DOCUMENTS

| | | | | |
|---|---|---|---|---|
| TW | 202015658 A | | 5/2020 | |
| WO | WO 2014/121211 A2 | | 8/2014 | |
| WO | WO-2017142876 A1 | * | 8/2017 | ........... A61K 31/105 |
| WO | WO-2018183929 A1 | * | 10/2018 | ......... A61B 10/0045 |
| WO | WO 2019/209787 A1 | | 10/2019 | |

OTHER PUBLICATIONS

International Search Report and Written Opinion for International Application No. PCT/US2020/029980, dated Aug. 14, 2020, 14 pages.

Mao et al., “A novel liposomal formulation of FTY720 (fingolimod) for promising enhanced targeted delivery,” Nanomedicine, Feb. 2014 (Epub Aug. 20, 2013);10(2):393-400.

Peine et al., “Liposomal resiquimod for the treatment of Leishmania donovani infection,” J Antimicrob Chemother, Jan. 2014 (Epub Aug. 16, 2013);69(1):168-175.

Zhang et al., “Long-acting liposomal corneal anesthetics,” Biomaterials, Oct. 2018 (Epub Aug. 9, 2018);181:372-377.

Engudar et al., “Remote loading of liposomes with a $^{124}$I-radioiodinated compound and their in vivo evaluation by PET/CT in a murine tumor model,” Theranostics, Nov. 12, 2018;8(21):5828-5841.

Li et al., “Accelerated Blood Clearance of Pegylated Liposomal Topotecan: Influence of Polyethylene Glycol Grafting Density and Animal Species,” J Pharm Sci, 2012;101(10):3864-3876.

* cited by examiner

LIPOSOMAL SUSTAINED-RELEASE COMPOSITIONS CONTAINING A THERAPEUTIC DRUG AND USE THEREOF

RELATED APPLICATIONS

This application is a national stage filing under 35 U.S.C. § 371 of International Application No. PCT/US2020/029980, filed Apr. 25, 2020, and designating the U.S., which claims the benefit of U.S. Provisional Application No. 62/838,571, filed Apr. 25, 2019, the contents of each of which are incorporated by reference in their entirety.

BACKGROUND

Technical Field

The present disclosure relates to a drug delivery system for delivery of a therapeutic drug. The present disclosure also relates to a pharmaceutical composition that has an improved release profile.

Description of Related Art

Liposomes are self-assembled, lipid based vesicles composed of phospholipid bilayers with an aqueous interior. These vesicles have been utilized as drug carriers for sustained drug delivery for decades. Liposomes as drug delivery vehicles alter the pharmacokinetic profile of the drug, which is usually reflected in the properties of slow drug release systemically or at the disease site, high administered doses with less frequent drug administration, and reduced side effects and toxicity with respect to a portion of drugs.

A liposomal drug formulation can be tailored to achieve slow drug release in vivo, which would prolong the therapeutic effect of the drug. However, multiple factors might affect the properties of the liposomes, such as the type of phospholipids used, phospholipid to cholesterol ratio, trapping agent used for drug loading, and possibly the lamellarity of the liposome.

A trend of prolonged release is projected in a direction such that the higher the drug per unit of used lipid in the liposomal composition is, the longer the drug remains in the lipid based vehicles of the liposomal composition (Johnston et al., Biochim Biophys Acta. 2006 January;1758(1):55-64, Chountoulesi et al., J Liposome Res. 2018 September;28 (3):249-258, and Johnston et al. Journal of Liposome Research, 18:145-157, 2008). Thus, a desired sustained-release liposomal composition should possess a high drug to lipid ratio. Nevertheless, the increased amount of a therapeutic agent, especially a highly potent drug, will raise the potential of enhanced side effects or undesired toxicity.

There is therefore an unmet need in the art for a beneficial and effective lipid based delivery system for a highly potent drug that has an improved release profile and lower undesired side effects or toxicity. The compositions and methods of the present disclosure satisfy these and other needs.

SUMMARY

The present disclosure provides a liposomal sustained-release composition, comprising a pharmaceutically effective amount of a therapeutic agent, and one or more lipids, wherein the therapeutic agent and total lipids are present at a predetermined ratio, whereby the liposomal sustained-release composition has a prolonged release profile of the therapeutic agent compared to a composition having the therapeutic agent and one or more lipids at a ratio higher than the predetermined ratio.

To improve upon existing treatment paradigms for diseases and to take advantage of the benefits of slow, sustained drug release, we developed a liposomal sustained-release composition comprising liposome-entrapped therapeutic agent and a predetermined amount of free therapeutic agent in an aqueous suspension for enhanced treatment of disease with desired pharmacokinetics.

The present disclosure provides a liposomal sustained-release composition for use in the treatment of disease having the advantages of: achieving a therapeutic effect with a much lower drug dose, quicker onset of action, reducing adverse drug reactions and systemic effects, increasing the residence time of drug in the target site via sustained release from the liposomal drug formulation, decreasing the frequency of drug administration, and potentially improving patient outcomes and compliance. The drug dose of the liposomal sustained-release composition for treating disease can significantly increase the therapeutic effects when compared to the unformulated therapeutic agent.

In some embodiments, the predetermined ratio of the therapeutic agent to the total lipids ranges from 0.0001 mol/mol to 0.15 mol/mol, optionally 0.0001 mol/mol to 0.14 mol/mol, optionally 0.0001 mol/mol to 0.13 mol/mol, optionally 0.0001 mol/mol to 0.12 mol/mol, optionally 0.0001 mol/mol to 0.11 mol/mol, and optionally 0.0001 mol/mol to 0.1 mol/mol, optionally 0.0001 mol/mol to 0.09 mol/mol, optionally 0.0001 mol/mol to 0.08 mol/mol, optionally 0.0001 mol/mol to 0.07 mol/mol, optionally 0.0001 mol/mol to 0.06 mol/mol, optionally 0.0001 mol/mol to 0.05 mol/mol, optionally 0.0001 mol/mol to 0.04 mol/mol, optionally 0.0001 mol/mol to 0.03 mol/mol, optionally 0.0001 mol/mol to 0.02 mol/mol, and optionally 0.0001 mol/mol to 0.01 mol/mol.

In some embodiments, the pharmaceutically effective amount of the therapeutic agent ranges from 0.0001 mg/mL to 10 mg/mL, optionally 0.0001 mg/mL to 7.5 mg/mL, optionally 0.0001 mg/mL to 5 mg/mL, optionally 0.0001 mg/mL to 2.5 mg/mL, optionally 0.0001 mg/mL to 2 mg/mL, optionally 0.0001 mg/mL to 1 mg/mL, and optionally 0.0001 mg/mL to 0.5 mg/mL.

In some embodiments, the liposomal sustained-release composition comprises a phospholipid concentration ranging from about 0.01 mM to about 100 mM, optionally about 0.1 mM to about 100 mM, and optionally about 0.1 mM to about 60 mM.

In certain embodiments, the therapeutic agent could be, but is not limited to: an antineoplastic agent, an analgesic, an anesthetic, or an immune modulator.

In some embodiments, the antineoplastic agent is selected from the group consisting of antihormonals, antifolates, antimicrotubule agents, alkylating agents, antimetabolites, antibiotics, topoisomerase inhibitors, antivirals, and cytotoxic agents.

In some embodiments, the antineoplastic agent is selected from the group consisting of vinca alkaloids, auristatins, cryptophycins, maytansines, anthracyclines, calicheamicins, duocarymycins, pyrrolobenzodiazepine (PBD) dimers, and α-amanitin.

In some embodiments, the analgesic is an α-adrenergic receptor (α-AR) agonist, an opioid, a nonsteroidal anti-inflammatory drug (NSAID), or a N-methyl-D-aspartate (NMDA) receptor antagonist.

In some embodiments, the α-AR agonist is an $\alpha_2$-AR agonist.

In some embodiments, the analgesic is selected from the group consisting of dexmedetomidine, clonidine, morphine, fentanyl, hydromorphone, codeine, oxycodone, hydrocodone, tramadol, ondansetron, dexamethasone, methadone, alfentanil, remifentanil, aspirin, ibuprofen, naproxen, indomethacin, ibuprofen, naproxen, fenoprofen, tolmetin, sulindac, meclofenamate, keoprofen, piroxicam, meloxicam, tenoxicam, droxicam, lornoxicam, flurbiprofen, diclofenac, acetylsalicylic acid, sodium acetylsalicylic acid, calcium acetylsalicylic acid, salicylic acid, sodium salicylate, dizocilpine, and ketamine.

In some embodiments, the anesthetic is an ester-based local anesthetic, an amide-based local anesthetic, an α-AR agonist, an opioid, a barbiturate compound, a benzodiazepine compound, or a NMDA receptor antagonist.

In some embodiments, the α-AR agonist is an $\alpha_2$-AR agonist.

In some embodiments, the anesthetic is selected from the group consisting of benzocaine, chloroprocaine, cocaine, cyclomethycaine, dimethocaine, piperocaine, propoxycaine, procaine, proparacaine, tetracaine, articaine, bupivacaine, cinchocaine/dibucaine, etidocaine, levobupivacaine, lidocaine, mepivacaine, prilocaine, ropivacaine, trimecaine, saxitoxin, tetrodotoxin, menthol, eugenol, dexmedetomidine, clonidine, morphine, fentanyl, hydromorphone, oxycodone, sufentanil, buprenorphine, butorphanol, diamorphine, levorphanol, pethidine, dexamethasone, methadone, alfentanil, remifentanil, nalbuphine, oxymorphone, pentazocine, amobarbital, methohexital, thiamylal, thiopental, diazepam, lorazepam, midazolam, dizocilpine, and ketamine.

In some embodiments, the immune modulator is a toll-like receptor (TLR) agonist or a sphingosine 1-phosphate receptor agonist.

In some embodiments, the TLR agonist is a TLR7 agonist or a TLR8 agonist.

In certain embodiments, the immune modulator is an imidazoquinoline compound.

In some embodiments, the immune modulator is selected from the group consisting of resiquimod, imiquimod, gardiquimod, CL075, SM-011, isatoribine, SM-360320, fingolimod, ponesimod, siponimod, ozanimod, and ceralifimod.

In some embodiments, the therapeutic agent is a highly potent agent.

In some embodiments, the liposomal sustained-release composition according to the present disclosure comprises liposomes, wherein the liposomes entrap the therapeutic agent.

In some embodiments, the liposomes of the liposomal sustained-release composition have a mean particle diameter of from about 50 nm to about 400 nm. Suitable liposomes of the composition according to the present disclosure may comprise:

a lipid bilayer comprising one or more phospholipids, a sterol, and an optional polyethylene glycol (PEG)-modified lipid; and an aqueous interior encompassed by the lipid bilayer and entrapping the therapeutic agent.

In accordance with the present disclosure, the one or more phospholipids is selected from the group consisting of hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), phosphatidylethanolamine lipid, and a combination thereof.

In some embodiments, the liposomal sustained-release composition comprises PEG-modified lipid at a molar percentage ranging from 0.001 mol % to 10 mol % on the basis of the total phospholipids and sterol.

In some embodiments, the PEG-modified lipid comprises a PEG moiety with an average molecular weight ranging from about 500 g/mol to about 5,000 g/mol.

In some embodiments, the PEG-modified lipid is 1,2-distearoyl-sn-glycero-3-phosphoethanolamine-N-[methoxy (polyethyleneglycol)] (DSPE-PEG).

In some embodiments, the one or more phospholipids of the liposomal sustained-release composition is a neutral phospholipid and the DSPE-PEG of the liposome is present in the composition at a molar percentage ranging from about 0.001 mol % to about 6 mol % on the basis of the total phospholipid and sterol.

In some embodiments, the molar ratio of the total phospholipids to sterol ranges from about 1:1 to about 3:1.

In some embodiments, the therapeutic agent is entrapped inside the liposome in the aqueous interior space of the liposome via a transmembrane pH gradient-driven remote loading method using a trapping agent.

In some embodiments, the trapping agent is ammonium sulfate, ammonium mesylate, ammonium tosylate, triethylammonium sucrose octasulfate, dextran sulfate, or a combination thereof.

In some aspects, the present disclosure provides a pharmaceutical composition for use in a treatment of a disease, which comprises a pharmaceutically effective amount of the liposomal sustained-release composition in accordance with the present disclosure, wherein the disease is selected from the group consisting of cancer, infectious disease, and autoimmune disease.

In some embodiments, the liposomal sustained-release composition is administered at a daily therapeutic dose of the therapeutic agent of not more than 10 mg/day. In some embodiments, the composition is administered by single, double, or multiple (e.g., three or more) administrations. In some embodiments, the composition is administered weekly, biweekly, or monthly.

In another aspect, the present disclosure provides a method for treating cancer, infectious disease, and/or autoimmune disease, the method comprising: administering a pharmaceutically effective amount of the liposomal sustained-release composition of the present disclosure.

In some embodiments, the liposomal sustained-release composition is administered at a daily therapeutic dose of the therapeutic agent of not more than 10 mg by single, double, or multiple (e.g., three or more) administrations weekly, biweekly, or monthly.

In yet another aspect, the present disclosure provides a method for controlling release of a therapeutic agent, comprising steps of:

introducing a liposomal composition into an environment, wherein the composition comprises:

a pharmaceutically effective amount of a therapeutic agent, and one or more lipids, wherein the therapeutic agent to the total lipids is at a predetermined ratio, the liposomal composition has a prolonged release profile of the therapeutic agent compared to a composition having the therapeutic agent and one or more lipids at a ratio higher than the predetermined ratio.

Other objectives, advantages, and novel features of the disclosure will become apparent from the following detailed description when taken in conjunction with the accompanying drawings.

DETAILED DESCRIPTION OF THE EMBODIMENTS

Figure 1A:
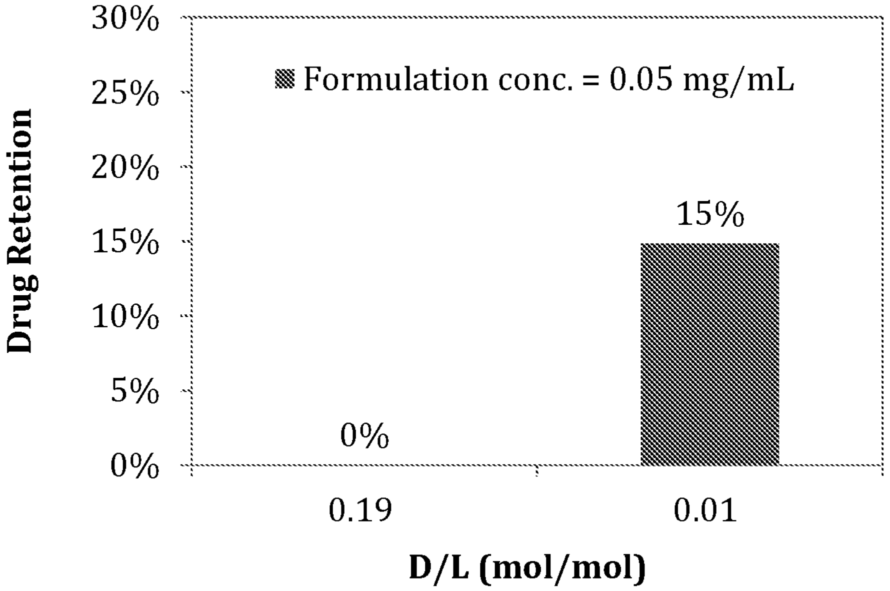
FIGS. 1A and 1B are graphs showing drug retention of liposomal compositions comprising resiquimod as the therapeutic agent with a formulation concentration of 0.05 mg/mL in 90% human plasma (the therapeutic agent concentration in 90% human plasma is 0.005 mg/mL) (FIG. 1A) or in 10% human plasma (the therapeutic agent concentration in 10% human plasma is 0.005 mg/mL) (FIG. 1B).

As employed above and throughout the disclosure, the following terms, unless otherwise indicated, shall be understood to have the following meanings.

As used herein, the singular forms "a", "an," and "the" include the plural reference unless the context clearly indicates otherwise.

All numbers herein may be understood as modified by "about," which, when referring to a measurable value such as an amount, a temporal duration, and the like, is meant to encompass variations of ±10%, ±5%, ±1%, or ±0.1% from the specified value, as such variations are appropriate to obtain a desired amount of liposomal drug, unless otherwise specified.

The term "treating," "treated," or "treatment" as used herein includes preventive (e.g., prophylactic), palliative, and curative uses or results.

The term "pharmaceutically effective amount" as used herein denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The term "pharmaceutically effective amount" also encompasses the amounts which are effective for increasing normal physiological function. In a particular embodiment, the pharmaceutically effective amount can be 0.005 $mg/m^2$/day to 3 $mg/m^2$/day, optionally 0.08 $mg/m^2$/day to 1 $mg/m^2$/day, and optionally 0.3 $mg/m^2$/day to 1 $mg/m^2$/day.

The term "subject" includes a vertebrate having cancer and/or a disease affecting pulmonary function. In some embodiments, the subject is a warm-blooded animal, such as a mammal, including a human.

As used herein, the term "drug to lipid ratio" ("D/L") refers to the ratio of therapeutic agent to total lipids. The content of therapeutic agent in a free form or liposomal form was determined by UV-Vis absorbance measurements. The phospholipid content or concentration of liposome and liposomal drug was determined by assaying the phosphorus content of liposome and liposomal drug samples using a phosphorus assay (adapted from G. Rouser et al., Lipids 1970, 5, 494-496).

As used herein, the term "mol %" means the percentage of moles of a given component of a mixture relative to the total moles of that mixture.

Liposome

The term "liposome" as used herein refers to a particle characterized by having an aqueous interior space sequestered from an outer medium by a membrane of one or more bilayer membranes forming a vesicle. Bilayer membranes of liposomes are typically formed by lipids, i.e., amphiphilic molecules of synthetic or natural origin that comprise spatially separated hydrophobic and hydrophilic domains. In certain embodiments of the present disclosure, the term "liposomes" refers to small unilamellar vesicle (SUV) liposomes in which one lipid bilayer forms the membrane.

In general, liposomes comprise a lipid mixture typically including one or more lipids selected from the group consisting of: dialiphatic chain lipids, such as phospholipids; diglycerides; dialiphatic glycolipids; single lipids such as sphingomyelin and glycosphingolipid; steroids such as cholesterol and derivatives thereof and a combination thereof.

Examples of phospholipids according to the present disclosure include, but are not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-gly cero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE).

Polyethylene Glycol (PEG)-Modified Lipid

A polyethylene glycol-modified lipid comprises a polyethylene glycol moiety conjugated to a lipid. In some embodiments, the PEG moiety has a molecular weight from about 500 to about 20,000 daltons. In some embodiments, the PEG-modified lipid is mixed with the phospholipids to form liposomes with one or more bilayer membranes. In some embodiments, the amount of PEG-modified lipid ranges from 0.0001 mol % to 40 mol %, optionally from 0.001 mol % to 30 mol %, and optionally from 0.01 mol % to 20 mol %, on the basis of the total phospholipids and sterol. In some embodiments, the amount of PEG-modified lipid is no more than 6 mol %, no more than 5 mol %, no more than 3 mol %, or no more than 2 mol %, on the basis of the total phospholipids and sterol. In some embodiments, the PEG-modified lipid has a PEG moiety with an average molecular weight ranging from 500 g/mol to 5,000 g/mol. In some embodiments, the PEG-modified lipid is phosphatidylethanolamine lipid linked to a polyethylene glycol group (PEG-PE). In some embodiments, phosphatidylethanolamine lipid includes is but not limited to 1,2-distearoyl-sn-glycero-3-phosphoethanolamine. In some embodiments, PEG-modified phosphatidylethanolamine is 1,2-distearoyl-sn-glycero-3-phosphoethanolamine-N-[methoxy(polyethylene glycol)] (DSPE-PEG).

Liposomal Sustained-Release Compositions

The terms "liposomal drug formulation," "liposomal composition," and "liposomal sustained-release composition" are used interchangeably in the present disclosure. The liposomal sustained-release composition in accordance with the present disclosure includes, but is not limited to, liposomes with entrapped therapeutic agent prepared by entrapping the therapeutic agent in the aqueous interior of the liposome via pass loading or a transmembrane pH gradient-driven remote loading method. In some embodiments, the transmembrane pH gradient is created by using a trapping agent for remote loading of the therapeutic agent into liposomes. In various embodiments, the trapping agent is selected from the group consisting of ammonium sulfate, ammonium mesylate, ammonium tosylate, triethylammonium sucrose octasulfate, dextran sulfate, and a combination thereof.

In certain embodiments, the liposome with the entrapped therapeutic agent comprises (a) a lipid bilayer comprising one or more phospholipids, a sterol, and a polyethylene glycol (PEG)-modified lipid, including but not limited to a PEG-modified phosphatidylethanolamine; and (b) an aqueous interior encompassed by the lipid bilayer entrapping a therapeutic agent.

In some embodiments, the one or more phospholipids is a neutral phospholipid. In some embodiments, the PEG-modified lipid is DSPE-PEG and the amount of DSPE-PEG in the liposome ranges from 0.001 mol % to 6 mol % on the basis of the total phospholipid and sterol.

In some embodiments, the liposomes with the entrapped therapeutic agent have a mean particle diameter between 50 nm and 400 nm.

Therapeutic Agents

The term "therapeutic agent" as used herein includes a substance that alleviates a symptom of or prevents development of a disease or disorder.

In one aspect, therapeutic agents according to the present disclosure refer to substances that are prescribed at the lowest effective dosage, with a dosing regimen given an adequate trial, and with the patient carefully followed with periodic determinations made about the need for continued therapy. Suitable therapeutic agents may be, but are not limited to: a growth factor, an immune modulator, an anti-inflammatory compound, an antibiotic, a compound that promotes angiogenesis, a compound that inhibits angiogenesis, a chemotactic agent, an agent that promotes apoptosis, an agent that inhibits apoptosis, a mitogenic agent, an analgesic, an anesthetic, an anti-coagulation agent, a procoagulation agent, and/or a contrast agent for imaging studies.

In some embodiments, the therapeutic agents may also include those active agents that are to be administered for long-term maintenance to patients such as cardiovascular drugs, including blood pressure, pacing, anti-arrhythmia, beta-blocking drugs, and calcium channel based drugs.

In some embodiments, the therapeutic agents may also include active agents for epilepsy or other movement disorders.

In some embodiments, these therapeutic agents may also include long-term medications such as contraceptives and fertility drugs. They could comprise neurologic agents such as dopamine and related drugs as well as psychological or other behavioral drugs. The therapeutic agents of the present disclosure may also include chemical scavengers such as chelators, antioxidants and nutritional agents.

In some embodiments, the therapeutic agent is directed to antineoplastic agents. A partial listing of the antineoplastic agents by classification is as follows.

Structure-based classes: fluoropyrimidines—5-fluorouracil, fluorodeoxyuridine, ftorafur, 5'-deoxyfluorouridine, UFT, S-1capecitabine; pyrimidine; nucleosides—deoxycytidine, cytosine arabinoside, 5-azacytosine, gemcitabine, 5-azacytosine-arabinoside; purines-6-mercaptopurine, thioguanine, azathioprine, allopurinol, cladribine, fludarabine, pentostatin, 2-chloro adenosine; platinum analogues—cisplatin, carboplatin, oxaliplatin, tetraplatin, platinum-DACH, ormaplatin, CI-973, JM-216; anthracyclines/anthracenediones—doxorubicin, daunorubicin, epirubicin, idarubicin, mitoxantrone; epipodophyllotoxins—etoposide, teniposide; camptothecins—irinotecan, topotecan, lurtotecan, silatecan, 9-amino camptothecin, 10,11-methylenedioxy camptothecin, 9-nitro camptothecin, TAS103, 7-(4-methyl-piperazino-methylene)-10,11-ethylenedioxy-20(s)-camptothecin, 7-(2-n-isopropylamino)ethyl)-20(s)-camptothecin; hormones and hormonal analogues—diethylstilbestrol, tamoxifen, toremefine, tolmudex, thymitaq, flutamide, bicalutamide, finasteride, estradiol, trioxifene, droloxifene, medroxyprogesterone acetate, megesterol acetate, aminoglutethimide, testolactone and others; vinca alkaloids—vincristine, vinblastine, vindesine, vinorelbine; taxanes—paclitaxel, docetaxel, abraxane, taxotere.

Mechanism-based classes: antihormonals—see classification for hormones and hormonal analogues, anastrozole; antifolates—methotrexate, aminopterin, trimetrexate, trimethoprim, pyritrexim, pyrimethamine, edatrexate, MDAM; antimicrotubule agents—taxanes and vinca alkaloids; alkylating agents (classical and non-classical)—nitrogen mustards (mechlorethamine, chlorambucil, melphalan, uracil mustard), oxazaphosphorines (ifosfamide, cyclophosphamide, perfosfamide, trophosphamide), alkylsulfonates (busulfan), nitrosoureas (carmustine, lomustine, streptozocin), thiotepa, dacarbazine and others; antimetabolites—purines, pyrimidines and nucleosides, listed above; antibiotics—anthracyclines/anthracenediones, bleomycin, dactinomycin, mitomycin, plicamycin, pentostatin, streptozocin; topoisomerase inhibitors—camptothecins (topo I), epipodophyllotoxins, m-AMSA, ellipticines (topo II); antivirals—AZT, zalcitabine, gemcitabine, didanosine, and others; miscellaneous cytotoxic agents—hydroxyurea, mitotane, fusion toxins, pyrazinamide, bryostatin, retinoids, butyric acid and derivatives, pentosan, fumagillin, and others.

In some embodiments, the therapeutic agent is an analgesic.

In certain embodiments, the analgesic can be, but not limited to, an α-adrenergic receptor (α-AR) agonist, an opioid, a nonsteroidal anti-inflammatory drug (NSAID) or a N-methyl-D-aspartate (NMDA) receptor antagonist.

In some embodiments, the α-AR agonist is an $\alpha_2$-AR agonist, such as dexmedetomidine.

In some embodiments, the analgesic is selected from the group consisting of dexmedetomidine, clonidine, morphine, fentanyl, hydromorphone, codeine, oxycodone, hydrocodone, tramadol, ondansetron, dexamethasone, methadone, alfentanil, remifentanil, aspirin, ibuprofen, naproxen, indomethacin, ibuprofen, naproxen, fenoprofen, tolmetin, sulindac, meclofenamate, keoprofen, piroxicam, meloxicam, tenoxicam, droxicam, lornoxicam, flurbiprofen, diclofenac, acetylsalicylic acid, sodium acetylsalicylic acid, calcium acetylsalicylic acid, salicylic acid, sodium salicylate, dizocilpine, and ketamine.

In some embodiments, the therapeutic agent is an anesthetic.

In certain embodiments, the anesthetic can be, but is not limited to, an ester-based local anesthetic, an amide-based local anesthetic, an α-AR agonist, an opioid, a barbiturate compound, a benzodiazepine compound, or a NMDA receptor antagonist.

In some embodiments, the α-AR agonist is an $\alpha_2$-AR agonist, such as dexmedetomidine.

In some embodiments, the anesthetic is selected from the group consisting of benzocaine, chloroprocaine, cocaine, cyclomethycaine, dimethocaine, piperocaine, propoxycaine, procaine, proparacaine, tetracaine, articaine, bupivacaine, cinchocaine/dibucaine, etidocaine, levobupivacaine, lidocaine, mepivacaine, prilocaine, ropivacaine, trimecaine, saxitoxin, tetrodotoxin, menthol, eugenol, dexmedetomidine, clonidine, morphine, fentanyl, hydromorphone, oxycodone, sufentanil, buprenorphine, butorphanol, diamorphine, levorphanol, pethidine, dexamethasone, methadone, alfentanil, remifentanil, nalbuphine, oxymorphone, pentazocine, amobarbital, methohexital, thiamylal, thiopental, diazepam, lorazepam, midazolam, dizocilpine, and ketamine.

In some embodiments, the therapeutic agent is an immune modulator.

In certain embodiments, the immune modulator is a toll-like receptor (TLR) agonist that induces innate immune activation.

In some embodiments, the therapeutic agent according to the present disclosure is a TLR7 agonist or a TLR8 agonist. Non-limiting examples of TLR7 agonists comprise resiquimod, imiquimod, gardiquimod, CL075, SM-011, the N9-pyridinylmethyl analogues recited in Jones et al., Bioorg Med Chem Lett. 2011 Oct. 1;21(19):5939-43 (as illustrated below), isatoribine, and SM-360320.

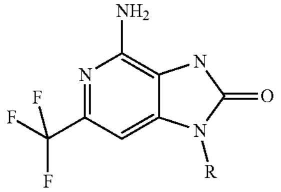

N9-pyridinylmethyl analogues

In certain embodiments, the immune modulator is a sphingosine 1-phosphate receptors (S1PR) agonist, which sequesters lymphocytes to peripheral lymphoid organs and away from the sites of chronic inflammation.

Non-limiting examples of S1PR agonists include fingolimod, ponesimod, siponimod, ozanimod, and ceralifimod.

In certain embodiments, the immune modulator is an imidazoquinoline compound.

Suitable imidazoquinoline compounds include, but are not limited to, resiquimod, imiquimod, gardiquimod, CL075, SM-011, and dactolisib.

The term "highly potent agent" refers to powerfully active pharmaceutical ingredients needing only very small quantities to exhibit a therapeutic effect. The highly potent agent in accordance to the present disclosure comprises active pharmaceutical ingredients with a daily therapeutic dose of not more than 10 mg/day.

In the field of pharmacology, potency is a measure of drug activity expressed in terms of the amount required to produce an effect of given intensity. A highly potent agent (e.g., fentanyl, alprazolam, risperidone) evokes a given response at low concentrations, while an active agent of lower potency evokes the same response only at higher concentrations.

In some embodiments, the highly potent agent according to the present disclosure includes, but is not limited to, microtubule disrupting agents, such as auristatins, cryptophycins and maytansines; and DNA modifying agents, such as anthracyclines, calicheamicins, duocarymycins, PBD dimers, and amanitins.

Non-limiting examples of the highly potent agent according to the present disclosure comprises vincristine, resiquimod, imiquimod, gardiquimod, fingolimod, dexmedetomidine, auristatins, cryptophycins, maytansines, anthracyclines, calicheamicins, duocarymycins, PBD dimers, and amanitins.

In various embodiments, the liposomal sustained-release composition according to the present disclosure has a predetermined ratio of the therapeutic agent to the total lipids ranging from 0.0001 mol/mol to 0.15 mol/mol, optionally 0.0001 mol/mol to 0.14 mol/mol, optionally 0.0001 mol/mol to 0.13 mol/mol, optionally 0.0001 mol/mol to 0.12 mol/mol, optionally 0.0001 mol/mol to 0.11 mol/mol, and optionally 0.0001 mol/mol to 0.1 mol/mol, optionally 0.0001 mol/mol to 0.09 mol/mol, optionally 0.0001 mol/mol to 0.08 mol/mol, optionally 0.0001 mol/mol to 0.07 mol/mol, optionally 0.0001 mol/mol to 0.06 mol/mol, optionally 0.0001 mol/mol to 0.05 mol/mol, optionally 0.0001 mol/mol to 0.04 mol/mol, optionally 0.0001 mol/mol to 0.03 mol/mol, optionally 0.0001 mol/mol to 0.02 mol/mol, and optionally 0.0001 mol/mol to 0.01 mol/mol.

Treatment of Diseases or Disorders

The liposomal sustained-release composition according to the present disclosure may be used to treat a disease or disorder according to a dosing regimens comprising administering to a mammal a pharmaceutically effective amount of the therapeutic agent as a unit dosage according to a continuous schedule, e.g., having a dosing interval selected from the group consisting of once-weekly dosing, twice-weekly dosing, thrice-weekly dosing, biweekly dosing, and bimonthly dosing.

In some embodiments, the liposomal sustained-release composition according to the present disclosure is for use in treatment of cancer or tumor including, but not limited to, lung cancer or tumor, breast cancer or tumor, liver cancer or tumor, hepatocellular carcinoma, pancreatic cancer or tumor, bowel and colon cancer or tumor, colorectal cancer or tumor, bladder cancer or tumor, ovarian cancer or tumor, prostate cancer or tumor, skin cancer or tumor, brain cancer or tumor, or malignancies affecting the bone marrow (including leukemias) and lymphoproliferative systems, such as Hodgkin's and non-Hodgkin's lymphoma.

In certain embodiments, the liposomal sustained-release composition according to the present disclosure comprises a TLR agonist that modulates toll-like receptor activity and is used in the treatment of neoplasia including, but not limited to, melanoma, basal cell carcinoma, squamous cell carcinoma, actinic keratosis, sarcomas, Kaposi's sarcoma, renal cell carcinoma, leukemias, myelogeous leukemia, chronic lymphocytic leukemia, and/or multiple myeloma.

In some embodiments, the liposomal sustained-release composition in accordance with the present disclosure is used in the treatment of infectious diseases including, but not limited to, viral infection such as genital warts, common warts, plantar warts, respiratory syncytial virus, hepatitis B, hepatitis C, Dengue virus, molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, parainfluenza, mumps virus, measles virus, papovavirus, hepadnavirus, flavivirus, retrovirus, arenavirus, and/or filovirus.

In some embodiments, the liposomal sustained-release composition in accordance with the present disclosure is used in the treatment of bacterial, fungal, and/or protozoal infections including, but not limited to, tuberculosis and *Mycobacterium avium*, leprosy, *Pneumocystis carinii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, or *Chlamydia*, or fungal infections such as candidiasis, aspergillosis, histoplasmosis, or cryptococcal meningitis.

In some embodiments, the liposomal sustained-release composition according to the present disclosure is used in the treatment of an autoimmune disease including, but not limited to, rheumatoid arthritis, systemic lupus erythematosus, multiple sclerosis, irritable bowel syndrome, Crohn's disease, inflammatory bowel disease (IBD), Hashimoto's thyroiditis, Graves' disease, Addison's disease, diabetes mellitus, idiopathic thrombocytopenic purpura, eosinophilic fasciitis, or antiphospholipid syndrome.

In some embodiments, the liposomal sustained-release composition according to the present disclosure is for use in pain relief or prevention of pain.

In some embodiments, the liposomal sustained-release composition according to the present disclosure is for use in anesthesia practice including, but not limited to, sedation, anxiety reduction, pain reduction, or delirium.

The disclosure will be further described with reference to the following specific, non-limiting examples.

EXAMPLES

The following examples illustrate the preparation and properties of certain embodiments of the present disclosure.

Example 1 Preparation of Liposomal Compositions

A. Preparation of Empty Liposomes

Liposomes were prepared via either a solvent injection method or a thin-film hydration method. The process for preparing empty liposomes using a solvent injection method is described as follows: HSPC, cholesterol and DSPE-mPEGr000 were mixed at a molar ratio of 3:2:0.045-0.3 and then were dissolved in absolute ethanol at 50 to 65° C. in a glass vial. The lipid solution was placed in a sonication bath to complete the lipid dissolution. Afterwards, the lipid solution was injected into a trapping agent solution under stirring (500 rpm) at 55 to 65° C., where the volume of the trapping agent solution is 4 to 10 times of the volume of lipid solution and the trapping agent solution can be 250 mM to 300 mM of ammonium sulfate, 300 mM ammonium sulfate in combination with 0.3 mM dextran sulfate, or 75 mM to 124 mM of triethylamine sucrose octasulfate to form a pro-liposome suspension. The obtained pro-liposome suspension was stirred (500 rpm) at 55 to 65° C. for 10 min followed by extruding for 5 to 10 times through a 0.2 μm polycarbonate membrane and then 3 to 5 times through a 0.1 μm polycarbonate membrane at 65° C. until the liposomes were in the size range of 90 to 160 nm. The liposome suspension was then dialyzed against a 9.4% (w/v) sucrose solution or saline using Float-A-Lyzer® dialysis devices (Spectra/Por®, MWCO: 50 kDa) at 4° C. under stirring (100 rpm) to remove the external trapping agents and ethanol. The volume of the dialysis solution was 100 times of the liposome suspension in each dialysis batch and three dialysis batches were applied at intervals of 12 hours. The resulting liposome suspension was filtered through a 0.2 μm polytetrafluoroethylene (PTFE) membrane to obtain the sterilized empty liposomes. The various formulations of empty liposomes prepared for drug loading are listed in Table 1.

TABLE 1

Liposome formulations

| Formulation | Lipids (molar ratio) HSPC | Cholesterol | DSPE-$mPEG_{2000}$ | Trapping agent solution |
|---|---|---|---|---|
| I | 3 | 2 | 0.045 | 300 mM ammonium sulfate |
| II | 3 | 2 | 0.3 | 250 mM ammonium sulfate |
| III | 3 | 2 | 0.045 | 300 mM ammonium sulfate/0.3 mM dextran sulfate |
| IV | 3 | 2 | 0.045 | 75 mM triethylamine sucrose octasulfate |
| V | 3 | 2 | 0.045 | 123.5 mM triethylamine sucrose octasulfate |

B. Drug Loading into Liposomes to Obtain Liposomal Compositions

Therapeutic agent as identified below was dissolved in 9.4% (w/v) sucrose or saline at the concentration of 20 mg/mL as a stock solution. Hydrochloric acid (HCl) was added into the therapeutic agent stock solution (to a final concentration up to 0.5 N) to accelerate therapeutic agent dissolution if necessary. L-histidine (L-His) buffer stock solution was prepared at the concentration of 31 mg/mL in 9.4% (w/v) sucrose or saline and was adjusted to pH 6.0 to 7.8 using 6 N HCl. Drug loading was performed by mixing the empty liposomes (prepared in Example 1-A), therapeutic agent stock solution, L-His stock solution, and 9.4% (w/v) sucrose or saline in a predetermined amount to result in a certain drug to lipid ratio (D/L) and followed by incubation at 20 to 60° C. for 30 min to obtain the liposomal composition. Liposomal compositions with D/L higher than 0.15 mol/mol were prepared as comparison examples. The drug loading profiles for some embodiments of the liposomal compositions are listed in Table 2 to Table 5.

C. Encapsulation Efficiency (EE) Analysis of Liposomal Compositions

The free form and liposomal form of therapeutic agent in the obtained liposomal compositions were separated by size exclusion chromatography through Sepharose® CL-4B (GE Healthcare) or Sephadex® G-50 Fine (GE Healthcare) resins. 2 mL of gel was packed in one column and the gel was washed by $ddH_2O$ and mobile phase solution (e.g., 9.4% ((w/v)) sucrose, 9.4% ((w/v)) sucrose containing L-His or saline, etc.) for at least 5 column volumes, respectively. 0.1 or 0.2 mL of the liposomal composition was added to the column drop-wisely and evenly distributed on the surface of the gel. After the sample immersing to the gel, 0.45 mL of the mobile phase solution was added to wash the column, followed by adding 1 mL or 0.7 mL of mobile phase solution to elute the liposomal form of drugs. The encapsulation efficiency was determined by $$\frac{\text{amount of therapeutic agent in liposomal form}}{\text{amount of therapeutic agent in total form}} \times 100\%,$$

in which the total form (containing free form and liposomal form of therapeutic agent) was prepared by 10 times or 3.5 times dilution of the liposomal composition to the mobile phase solution. For concentration determination of the therapeutic agents, liposomal- and total form of therapeutic agents were mixed with 100% methanol (MeOH) where the volume of MeOH was at least 4 times of the samples. The mixtures were then sonicated for 10 min to break the liposomes and subsequently diluted with diluents if further dilution was needed. The assays of the therapeutic agents were performed either in HPLC or UV plate reader.

TABLE 2

Drug loading profiles of liposomal compositions with resiquimod as the therapeutic agent

| Sample name | D/L (mol/mol) | Drug conc. (mg/mL) | Empty liposome | L-His (pH 6.5) conc. (mM) |
|---|---|---|---|---|
| JCCR848-05 | 0.439 | 6 | Formulation I | 50 |
| JCCR848-06 | 0.146 | 2 | | |
| CHYR848-011 | 0.192 | 2 | | 20 |
| CHYR848-014 | 0.594 | 0.05 | Formulation II | 20 |
| CHYR848-015 | 0.198 | | | |
| CHYR848-016 | 0.059 | | | |
| CHYR848-017 | 0.020 | | | |
| CHYR848-018 | 0.010 | | | |
| CHYR848-019 | 0.005 | | | |
| CHYR848-020 | 0.594 | | | |
| CHYR848-021 | 0.198 | 0.5 | | |
| CHYR848-022 | 0.059 | | | |
| CHYR848-023 | 0.594 | 6 | | |
| CHYR848-024 | 0.198 | 2 | | |
| CHYR848-025 | 0.059 | 0.6 | | |
| CHYR848-026 | 0.020 | 0.2 | | |
| CHYR848-027 | 0.010 | 0.1 | | |
| CHYR848-029 | 0.576 | 1 | Formulation III | 20 |
| CHYR848-030 | 0.192 | | | |
| CHYR848-031 | 0.096 | | | |
| CHYR848-032 | 0.058 | | | |
| CHYR848-033 | 0.576 | 0.1 | | |
| CHYR848-034 | 0.192 | | | |
| CHYR848-035 | 0.096 | | | |
| CHYR848-036 | 0.058 | | | |
| CHYR848-037 | 0.019 | | | |
| CHYR848-038 | 0.010 | | | |
| CHYR848-039 | 0.005 | | | |

TABLE 3

Drug loading profiles of liposomal sustained-release compositions with imiquimod as the therapeutic agent

| Sample name | D/L (mol/mol) | Drug conc. (mg/mL) | Empty liposome | L-His (pH 6.5) conc. (mM) |
|---|---|---|---|---|
| CHYIMQ-009 | 0.502 | 4 | Formulation I | 10 |
| CHYIMQ-010 | 0.754 | 1 | | |
| CHYIMQ-011 | 0.251 | 1 | | |
| CHYIMQ-012 | 0.126 | 1 | | |

TABLE 3-continued

Drug loading profiles of liposomal sustained-release compositions with imiquimod as the therapeutic agent

| Sample name | D/L (mol/mol) | Drug conc. (mg/mL) | Empty liposome | L-His (pH 6.5) conc. (mM) |
|---|---|---|---|---|
| CHYIMQ-013 | 0.075 | 1 | | |
| CHYIMQ-014 | 0.025 | 0.1 | | |
| CHYIMQ-015 | 0.013 | 0.1 | | |

TABLE 4

Drug loading profiles of liposomal sustained-release compositions with fingolimod as the therapeutic agent

| Sample name | D/L (mol/mol) | Drug conc. (mg/mL) | Empty liposome | L-His (pH 7.0) conc. (mM) |
|---|---|---|---|---|
| JCCFIN18 | 0.196 | 2 | Formulation I | 50 |
| JCCFIN19 | 0.393 | 4 | | |
| JCCFIN20 | 0.589 | 6 | | |
| JCCFIN04 | 0.785 | 8 | | |
| CHYFIN01 | 0.589 | 1 | | |
| CHYFIN02 | 0.196 | 1 | | |
| CHYFIN03 | 0.098 | 1 | | |
| CHYFIN04 | 0.059 | 1 | | |
| CHYFIN05 | 0.020 | 0.1 | | |
| CHYFIN06 | 0.010 | 0.1 | | |

TABLE 5

Drug loading profiles of liposomal sustained-release compositions with dexmedetomidine as the therapeutic agent

| Sample name | D/L (mol/mol) | Drug conc. (mg/mL) | Empty liposome | L-His (pH 6.5) conc. (mM) |
|---|---|---|---|---|
| YW4_NL | 0.241 | 2 | Formulation I | 10 |
| CHYDEX01 | 0.904 | 1 | | |
| CHYDEX02 | 0.301 | 1 | | |
| CHYDEX03 | 0.15 | 1 | | |
| CHYDEX04 | 0.090 | 1 | | |
| CHYDEX05 | 0.030 | 0.1 | | |
| CHYDEX06 | 0.015 | 0.1 | | |

Example 2 In Vitro Release Profiles of Liposomal Compositions

Diafiltration using Amicon® Ultra-0.5 Centrifugal Filter Devices (50 kDa, Millipore®) can be performed prior to in vitro release experiments if the encapsulation efficiencies of the liposomal compositions were less than 70%.

9.4% sucrose containing 20 mM of L-His buffer was used as a diluent for dilution of liposomal compositions if different formulation concentrations were applied with the same D/L liposomal composition. The in vitro release profiles of the liposomal composition were carried out by mixing liposomal compositions and release medium. The dilution factor of the liposomal compositions in release medium was ten in all in vitro release experiments. The release conditions were either in 90% human plasma or 10% human plasma at room temperature for 5 min. The encapsulation efficiencies of the liposomal compositions in 90% or 10% human plasma were analyzed as described in Example 1-C. Drug retention was calculated by $$\frac{EE \text{ of liposomal composition after in vitro release}}{EE \text{ of liposomal composition before in vitro release}} \times 100\%.$$

The liposomal compositions used in the in vitro release experiments, the release conditions and results are listed in Table 6. The release results are also shown in FIG. 1A to FIG. 3.

Figure 1B:
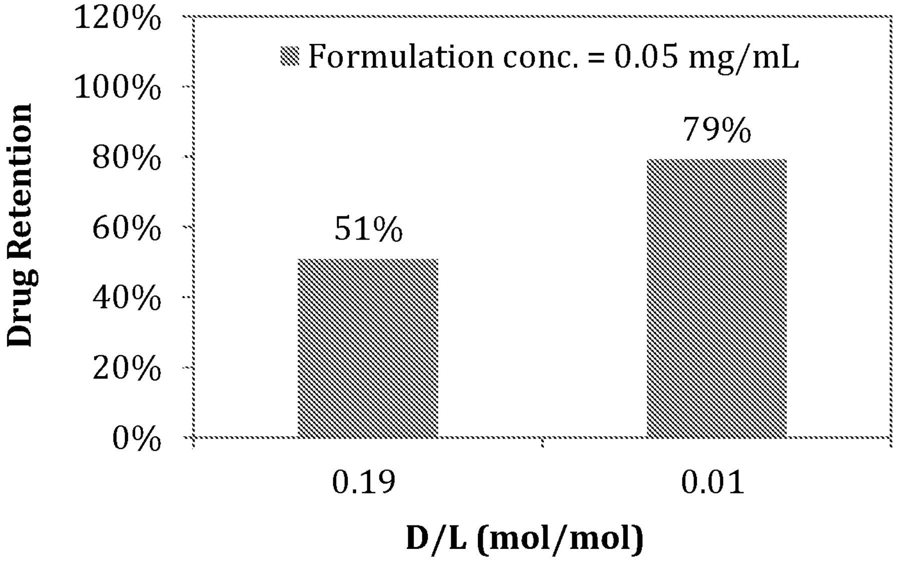

As illustrated in FIGS. 1A-1B, the results indicated that the lower the D/L, the better the drug retention ability of liposomal composition having resiquimod as the therapeutic agent. The results shown in FIG. 1A were acquired from the data of IVR01 (D/L=0.19 mol/mol) and IVR02 (D/L=0.01 mol/mol), and the results shown in FIG. 1B were acquired from the data of IVR04 (D/L=0.19 mol/mol) and IVR05 (D/L=0.01 mol/mol) listed in Table 6.

Figure 2:
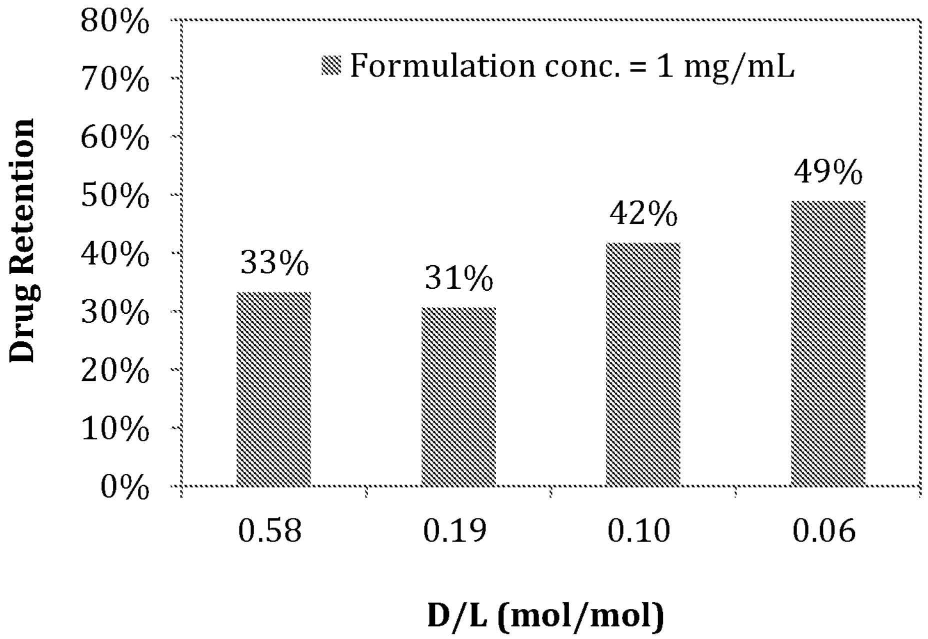
FIG. 2 is a graph showing drug retention of liposomal compositions comprising resiquimod as the therapeutic agent with a formulation concentration of 1 mg/mL in 90% human plasma, whereby the final therapeutic agent concentration in 90% human plasma is 0.1 mg/mL.

FIG. 2 demonstrates the same trend of drug retention ability as FIGS. 1A-1B: the lower the D/L (when D/L<0.19 mol/mol), the better the drug retention ability of liposomal composition having resiquimod as the therapeutic agent. The results shown here were acquired from the data of IVR13 (D/L=0.58 mol/mol), IVR14 (D/L=0.19 mol/mol), IVR15 (D/L=0.10 mol/mol), and IVR16 (D/L=0.06 mol/mol) listed in Table 6.

Figure 3:
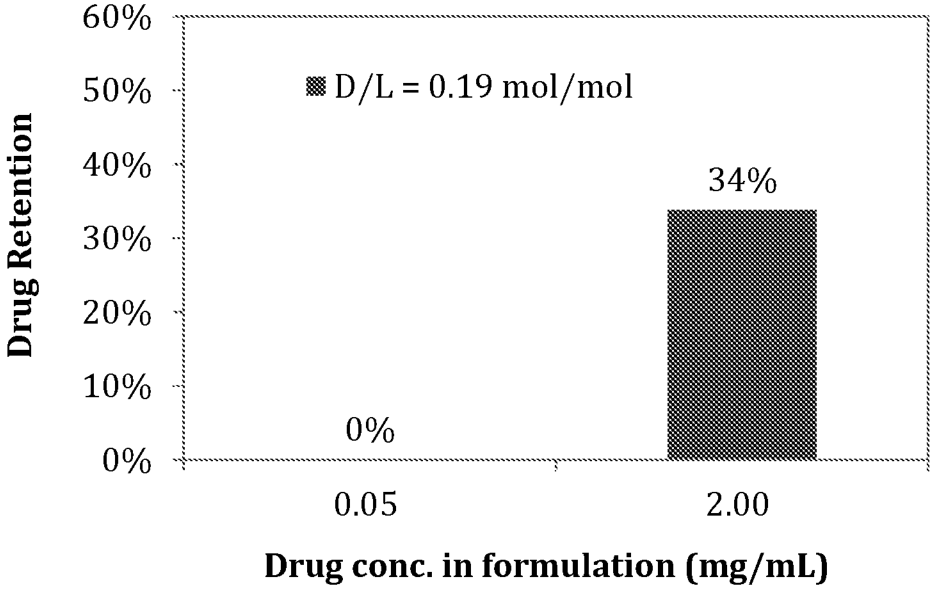
FIG. 3 is a graph depicting drug retention of liposomal compositions comprising resiquimod as the therapeutic agent with a fixed drug to lipid ratio of 0.19 mol/mol (D/L=0.19 mol/mol) in 90% human plasma (the formulation concentration of the therapeutic agent is 0.05 mg/mL or 2.00 mg/mL and the therapeutic agent concentration in 90% human plasma is 0.005 mg/mL or 0.2 mg/mL, respectively).

Referring to FIG. 3, the results indicate that a liposomal composition having high D/L (0.19 mol/mol) exhibits poor drug retention in human plasma when applied in low concentration (0.05 mg/mL). The results shown in FIG. 3 were acquired from the data of IVR01 (drug conc.=0.05 mg/mL) and IVR12 (drug conc.=2.00 mg/mL) listed in Table 6.

TABLE 6

Conditions and results of in vitro release experiments

| IVR trial no. | Sample | D/L (mol/mol) | Resiquimod conc. in formulation (mg/mL) | Resiquimod conc. in release medium (mg/mL) | Release medium | Drug retention (%) |
|---|---|---|---|---|---|---|
| IVR01 | CHYR848-011 | 0.192 | 0.05 | 0.005 | 90% human plasma | 0.0 |
| IVR02 | CHYR848-018 | 0.01 | 0.05 | 0.005 | | 14.9 |
| IVR03 | CHYR848-011 | 0.192 | 1 | 0.1 | | 44.3 |
| IVR04 | CHYR848-011 | 0.192 | 0.05 | 0.005 | 10% human plasma + 80% PBS | 50.9 |
| IVR05 | CHYR848-018 | 0.01 | 0.05 | 0.005 | | 79.2 |
| IVR06 | CHYR848-011 | 0.192 | 1 | 0.1 | | 89.6 |
| IVR10 | CHYR848-020 | 0.594 | 1 | 0.1 | 90% human plasma | 21.2 |
| IVR11 | CHYR848-024 | 0.198 | 1 | 0.1 | | 20.5 |
| IVR12 | CHYR848-024 | 0.198 | 2 | 0.2 | | 33.8 |
| IVR13 | CHYR848-029 | 0.576 | 1 | 0.1 | | 33.2 |
| IVR14 | CHYR848-030 | 0.192 | 1 | 0.1 | | 30.6 |
| IVR15 | CHYR848-031 | 0.096 | 1 | 0.1 | | 41.7 |
| IVR16 | CHYR848-032 | 0.058 | 1 | 0.1 | | 48.8 |

What is claimed is:

1. A liposomal sustained-release composition, comprising:

a liposome and a pharmaceutically effective amount of an imidazoquinoline compound, wherein the liposome comprises a lipid bilayer comprising one or more lipids, and an aqueous interior encompassed by the lipid bilayer and entrapping the imidazoquinoline compound, wherein the imidazoquinoline compound is selected from the group consisting of resiquimod, imiquimod, gardiquimod, CL075, and SM-011, and wherein the imidazoquinoline compound and total lipids are present in the liposomal sustained-release composition at a predetermined ratio ranging from 0.0001 mol/mol to 0.15 mol/mol.

2. The liposomal sustained-release composition of claim 1, wherein the pharmaceutically effective amount of the imidazoquinoline compound ranges from 0.0001 mg/mL to 10 mg/mL.

3. The liposomal sustained-release composition of claim 1, wherein the composition has a phospholipid concentration ranging from about 0.01 mM to about 100 mM.

4. The liposomal sustained-release composition of claim 1, wherein the imidazoquinoline compound is in a daily therapeutic dose of not more than 10 mg/day.

5. The liposomal sustained-release composition of claim 1, wherein the liposome has a mean particle diameter of from about 50 nm to about 400 nm.

6. The liposomal sustained-release composition of claim 1, wherein the lipid bilayer comprises one or more phospholipids, a sterol, and an optional polyethylene glycol (PEG)-modified lipid.

7. The liposomal sustained-release composition of claim 6, wherein the one or more phospholipids are selected from the group consisting of hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), phosphatidylethanolamine lipid, 1,2-dimyristoyl-sn-glycero-3-phosphocholine (DMPC), 1,2-dioleoy1-sn-glycero-3-phosphocholine (DOPC) and a combination thereof.

8. The liposomal sustained-release composition of claim 6, wherein the PEG-modified lipid is present at a molar percentage ranging from 0.001 mol % to 10 mol % on the basis of the total phospholipids and sterol.

9. The liposomal sustained-release composition of claim 6, wherein the PEG-modified lipid has a PEG moiety with an average molecular weight ranging from about 500 g/mol to about 5,000 g/mol.

10. The liposomal sustained-release composition of claim 6, wherein the PEG-modified lipid is 1,2-distearoyl-sn-glycero-3-phosphoethanolamine-N-[methoxy(polyethylene glycol)] (DSPE-PEG).

11. The liposomal sustained-release composition of claim 10, wherein the one or more phospholipids is a neutral phospholipid and wherein the DSPE-PEG of the liposome is present at a molar percentage ranging from about 0.001 mol % to about 6 mol % on the basis of the total phospholipids and sterol.

12. The liposomal sustained-release composition of claim 6, wherein the molar ratio of the total phospholipids to sterol ranges from about 1:1 to about 3:2.

13. The liposomal sustained-release composition of claim 1, wherein the imidazoquinoline compound is entrapped in the aqueous interior via a transmembrane pH gradient-driven remote loading method using a trapping agent.

14. The liposomal sustained-release composition of claim 13, wherein the trapping agent is ammonium sulfate, ammonium mesylate, ammonium tosylate, triethylammonium sucrose octasulfate, dextran sulfate, or a combination thereof.

15. A method for treating cancer, infectious disease, or autoimmune disease, comprising: administering a pharmaceutically effective amount of the liposomal sustained-release composition of claim 1.

16. The method of claim 15, wherein the imidazoquinoline compound is in a daily therapeutic dose of not more than 10 mg/day.

17. A method for controlling release of an imidazoquinoline compound, comprising:

introducing the liposomal sustained-release composition of claim 1 into an environment, whereby the liposomal sustained-release composition has a prolonged release profile of the imidazoquinoline compound compared to a composition comprising the imidazoquinoline compound and one or more lipids at a ratio higher than the predetermined ratio of the liposomal sustained-release composition of claim 1.

* * * * *